US005780064A

United States Patent [19]

Meisters et al.

[11] Patent Number: 5,780,064
[45] Date of Patent: Jul. 14, 1998

[54] GERMICIDAL COMPOSITIONS FOR THE TREATMENT OF ANIMAL INFECTIOUS DISEASES OF THE HOOF

[75] Inventors: George J. Meisters, Mount Prospect; Charles D. Gradle, Berwyn, both of Ill.

[73] Assignee: Babson Bros. Co., Naperville, Ill.

[21] Appl. No.: 938,013

[22] Filed: Sep. 12, 1997

[51] Int. Cl.$^6$ .......................... A61K 31/14; A61K 33/34; A61K 33/40

[52] U.S. Cl. .................. 424/616; 424/637; 514/643

[58] Field of Search .................. 424/637, 616; 514/643

[56] References Cited

U.S. PATENT DOCUMENTS

| | | | |
|---|---|---|---|
| 59,845 | 11/1866 | Kinney. | |
| 62,644 | 3/1867 | Lawes. | |
| 85,650 | 1/1869 | Eckert. | |
| 459,178 | 9/1891 | Gayman et al.. | |
| 811,718 | 2/1906 | Hatch. | |
| 1,067,757 | 7/1913 | Rawson. | |
| 2,917,428 | 12/1959 | Hitzman | 167/22 |
| 3,003,913 | 10/1961 | Rowe | 167/16 |
| 4,229,410 | 10/1980 | Kosti | 422/28 |
| 4,268,504 | 5/1981 | Harrington et al. | 424/143 |
| 4,311,598 | 1/1982 | Verachtert | 210/757 |
| 4,654,208 | 3/1987 | Stockel et al. | 424/78 |
| 4,774,075 | 9/1988 | Lang et al. | 424/47 |
| 4,796,646 | 1/1989 | Grollier et al. | 132/202 |
| 4,822,595 | 4/1989 | Corliss et al. | 424/61 |
| 4,828,819 | 5/1989 | Lan et al. | 424/47 |
| 4,895,722 | 1/1990 | Abe et al. | 424/71 |
| 4,923,677 | 5/1990 | Simon et al. | 422/37 |
| 4,952,398 | 8/1990 | Tapin | 71/67 |
| 4,997,625 | 3/1991 | Simon et al. | 422/29 |
| 5,080,888 | 1/1992 | Grollier et al. | 424/61 |
| 5,320,805 | 6/1994 | Kramer et al. | 422/28 |
| 5,332,511 | 7/1994 | Gay et al. | 210/755 |
| 5,373,025 | 12/1994 | Gay | 514/642 |
| 5,620,527 | 4/1997 | Kramer et al. | 134/2 |

OTHER PUBLICATIONS

NAHMS Dairy '96, "Digital Dermatitis on U.S. Dairy Operations", May 1997, 1–28, Booklet.
Burgi, "Real Answers to Solving the Problems of Digital Dermatitis", Jun. 1996, 1–3.
UC Davis, "Papillomatous Digital Dermatitis in Cattle", Feb. 1997, 1–3.
Maas, DVM, Fact Sheet No. 5: Footrot, Mar. 1996, 1–2.
Ames, "Update: Healing Hairy Heel Warts", Apr. 1997, 1–2.
SSI Corporation, HoofPro +pH Adjusted for Dairy Cattle, 1995, Advertisement.
ECOLAB, Oxy-Step: Or Simply Add Oxy-Step To Your Rotation, 1996, Advertisement.
Adapted from Weaver AD: Cattle Foot Problems Part I, Dairyguard Sanitizing Footbath, Jan.–Feb. 1988, 9:1, 34–38.
SSI Corporation, "Footbath Solution Disposal —HoofPro Suspended Copper vs. Conventional Copper", 1993.
Berry, "In–Parlor Spray Treatments for the Control of Foot-warts", Jun. 1997, 1–2.
UC Davis, Footwarts of Dairy Cattle, Jun. 1997, Research Sheet.

*Primary Examiner*—Phyllis G. Spivack
*Attorney, Agent, or Firm*—Lathrop & Clark

[57] ABSTRACT

An aqueous germicidal composition for the treatment or prevention of infectious diseases of the hoof in animals, comprising a copper salt, a quaternary ammonium compound, and a peroxide is disclosed. A method for treating or preventing infectious diseases of the hoof in animals, comprising topically administering an effective amount of an aqueous germicidal composition comprising a copper salt, a quaternary ammonium compound, and a peroxide is also disclosed.

29 Claims, No Drawings

GERMICIDAL COMPOSITIONS FOR THE TREATMENT OF ANIMAL INFECTIOUS DISEASES OF THE HOOF

FIELD OF THE INVENTION

The present invention relates to the treatment and prevention of infectious diseases of the hoof in animals.

BACKGROUND OF THE INVENTION

Infectious diseases of the hoof, such as hairy hoof warts (papillomatous digital dermatitis, or "PDD") hoof rot (interdigital phlegmon), and stable hoof rot (interdigital dermatitis) are common in farm animals such as sheep, goats, horses, dairy cows, and beef cattle. Hoof warts were first reported in Italy in 1974, and since that time, have spread throughout the world. Since the late 1980's, hoof warts have been a significant source of bovine lameness, and have had a large economic impact on the dairy industry. For example, a recent study by the U.S. Department of Agriculture concluded that 47% of all dairy herds in the United States are affected by PDD, with 78% of those herds reporting their first cases in 1993 or later. See *Digital Dermiatitis on U.S. Dairy Operations*, NAFMS Dairy Study, May, 1997.

Clinically, PDD appears as a lameness outbreak of variable severity within a specific animal herd. It is a superficial skin disease of the animal digit with variable presentation, depending on the stage of the lesion, from painful, moist, strawberry-like lesions to raised, hairy, wart-like lesions. It can result in severe lameness, and even death, if not properly treated. With respect to dairy cows, hoof warts are also associated with losses in milk production, reproductive efficiency, and body weight.

Although PDD was originally believed to be caused by a virus, it is now believed that PDD is caused by one or more bacteria. Researchers have isolated two different spirochete species of bacteria from numerous PDD lesions, but have been unable to replicate the infectious disease in healthy animals using purified cultures of these organisms, thus signifying that additional causative agents and/or environmental conditions are necessary to bring about the disease.

Hoof rot, or interdigital phlegmon, is an infection of the soft tissue between the claws of the feet. In equine animals, it is also known as hoof thrush. Here, the term "hoof rot" will be used to indicate both hoof rot and hoof thrush. Hoof rot is caused by the anaerobic bacterium, *Fusobacterium necrophorum*. The anaerobes *Dichelobacter (Bacteriodes) nodosus* and *Prevotella melaninogenicus* have also been implicated. The bacteria invade the skin of the foot at injured or damaged skin areas, and initially cause a painful swelling of the skin between the claws. A fissure or crack then develops along the swollen area for part or all of the length of the interdigital space. If left untreated, hoof rot can enter the joints, bones, and/or tendons of the foot, making recovery from the infection unlikely. Animals with hoof rot can have a mild fever, loss of appetite and accompanying weight loss, and develop mild to severe lameness.

Interdigital dermatitis, or stable hoof rot, is generally a chronic inflammation of the skin in the area between the toes of the feet (interdigital cleft). This infection is caused by the bacterium *Dichelobacter nodosus*. The skin in the area of the interdigital cleft will appear puffy with a dry exudation which will cause a crust to form. The condition may occasionally cause lameness or heel crack/heel erosion but generally results in an alteration in the animal's gait.

At present, hoof warts, hoof rot and stable hoof rot are treated in several ways. The most effective treatment is the use of antibiotics, such as tetracycline, lincomycin, spectinomycin, penicillin, oxytetracycline, and ampicillin, which are topically applied to the affected area via use of footbaths, sprays, or footwraps. While antibiotics are effective in treating these infectious diseases, there are several drawbacks associated with antibiotic use. Antibiotics are expensive, and there is concern, especially with dairy cows, that the use of antibiotics may result in the presence of antibiotic residues in the animal or its milk. Further, extended use of antibiotics may result in the development of an antibiotic-resistant bacteria strain. Finally, at present, the use of antibiotics for the treatment of hoof rot, stable hoof rot or PDD is "off-label," that is, the antibiotics are not specifically approved for these uses.

The use of chemical-based germicides has also been tried as a treatment to prevent and/or control hoof rot, hoof warts, and stable hoof rot. Although some germicides, such as those containing copper sulfate and zinc sulfate, have some efficacy against hoof rot and stable hoof rot, they are ineffective against hoof warts. Quaternary ammonium compounds have also been used, but have never been proven to be effective against PDD. Such compounds are in addition ineffective at high dilutions, such as those used in foot baths, and many are expensive. Likewise, combinations of hydrogen peroxide and peracetic acid have been used, but also are not effective against PDD, and suffer from stability and storage problems. This chemical combination is also irritating to the hoof at the recommended treatment concentrations.

There have been anecdotal reports of success with formaldehyde against PDD, but controlled trials indicate that formaldehyde is less effective than antibiotics. Additionally, formaldehyde is classified as a carcinogen and toxin, and is illegal in some parts of the United States. Further, use of too high a concentration of formaldehyde can result in destruction of healthy hoof tissue, or can even lead to sloughing of the hoof. Thus, the use of formaldehyde is neither feasible nor effective in treating foot rot, stable foot rot, and PDD.

As stated above, footbaths comprising a germicide, such as copper sulfate or hydrogen peroxide, or even an antibiotic, are commonly used to attempt to prevent hoof rot, stable hoof rot, and/or PDD. Foot baths are typically dilutions of spray or footwrap compositions. However, the germicide or antibiotic present in these footbaths can be easily overcome by the harsh environmental conditions to which the bath is subjected. As a result, these baths can become a breeding ground for bacteria, and can thus actually accelerate the spread of an infectious hoof disease, rather than prevent it.

Therefore, a need exists for a composition that is effective against foot rot, stable foot rot, and PDD, that is affordable, and that avoids the use of antibiotics. There is also a need for an effective method of both controlling and treating foot rot, stable foot rot, and PDD. There is a further need for a compostion that can be used in a footbaths effectively, and can withstand the harsh conditions associated with hoof baths. These needs are met by the composition and method of the present invention.

SUMMARY OF THE INVENTION

It has been surprisingly discovered that an aqueous germicidal composition comprising a copper salt, a quaternary ammonium compound, and a peroxide, is effective in treating and preventing PDD, even though none of these germicides have been proven effective against PDD by itself at any level of use. Moreover, although none of these germicides have been proven effective against PDD individually, in field tests involving dairy cattle afflicted with PDD, the above composition was as effective in treating PDD as the use of an antibiotic. Moreover, the composition of the present invention is more effective against hoof rot and stable hoof rot than any of the above compounds used individually, and is better able to withstand adverse foot bath conditions. Finally, the present invention also provides a method for the treatment of infectious diseases of the hoof in animals, comprising topically applying an effective amount of the above aqueous composition.

The composition and method of the present invention are effective under a wide variety of conditions and dilutions, are inexpensive to use, and have none of the disadvantages associated with the use of antibiotics.

DETAILED DESCRIPTION OF THE PREFERRED EMBODIMENTS

The Copper Salt

The copper salt of the present invention can be any water soluble copper salt, such as copper sulfate, copper benzoate, copper bicarbonate, copper nitrate, copper nitrite, copper chloride, copper acetate, copper formate, copper trichloroacetate, copper citrate, copper gluconate, and mixtures thereof. Other copper salts may be used, so long as the anion is biocidally acceptable and capable of solubilizing copper cations in water. The preferred copper salt for use in the compositions and method of the present invention is copper sulfate.

The copper salt should be present in an amount from about 2% by weight of the composition to the amount at which the composition becomes saturated and no more copper salt will dissolve. For copper sulfate, the solubility limit is approximately 20% copper sulfate by weight of the composition. Preferably, the copper salt is present in an amount from about 15% to about 20% by weight of the composition, where the range includes both 15% and 20% copper salt content.

The Quaternary Ammonium Compound

Any quaternary ammonium compound with germicidal activity can be used in the composition and method of the present invention. Useful quaternary ammonium compounds include alkyl, dialkyl, and trialkyl quaternary ammonium salts, where the alkyl groups contain from 1 to 20 carbon atoms in each alkyl group, and quaternary ammonium salts containing one or more substituted or unsubstituted aryl groups, or mixtures of the above quaternary ammonium salts. Quaternary ammonium chlorides are preferred, although other water dispersible salts, such as acetates, sulfates, nitrates, and phosphates, may also be used.

The preferred quaternary ammonium compound in the composition of the present invention is a mixture of N-Alkyl ($C_{12-18}$)-N,N-dimethyl benzylammonium chloride and N-Alkyl($C_{12-18}$)-N,N-dimethyl ethylbenzylammonium chloride, which is sold under the trade name BTC 2125 M, and is available from Stepan Company (Northfield, Ill.). Another preferred quaternary ammonium compound for use in the compositions of the present invention is a mixture of N-Alkyl($C_{12-18}$)-N,N-dimethyl-N-benzylammonium chloride, N-Dodecyl-N,N-dimethyl-N-ethylbenzylammonium chloride, and N-Tetradecyl-N,N-dimethyl-N-benzylammonium chloride, which is sold under the trade name Barquat 4280-Z by Lonza (Fair Lawn, N.J.).

The quaternary ammonium compound should be present in an amount from about 0.5% to about 2% by weight of the aqueous composition. Preferably, the quaternary ammonium compound should be present in an amount from about 1% to about 2% by weight of the composition.

The Peroxide

Any water-soluble peroxide can be used in the composition and method of the present invention. The preferred peroxide is hydrogen peroxide, and either concentrated or dilute aqueous solutions of hydrogen peroxide can be used. The peroxide should be present initially in an amount from about 0.5% to about 5% by weight in the aqueous compositions of the present invention. Over time, the amount of peroxide in the composition will slowly decrease, due to degradation. The preferred range of hydrogen peroxide for the composition of the present invention is from about 1% to about 2% by weight of the composition.

General Characteristics

The compositions of the present invention should have a pH sufficient to effect complete dissolution of the copper salt. The pH of the composition should thus be about 3 or less, with a pH from about 1.6 to about 2.0 being preferred. The aqueous germicidal composition should also be stable under general storage conditions. The viscosity of the composition can be varied depending on the use to be made of the composition, and can be made more viscous, if desired, through the use of known thickening agents.

Other Components

Other components may also be included in the aqueous germicidal compositions of the present invention. For example, pH adjusting agents can be used to adjust the pH of the composition to the desired level. Both mineral acids, organic acids, and mixtures thereof can be used for this purpose. Useful organic acids include hydroxyacetic acid, citric acid, and lactic acid, while mineral acids that can be used include phosphoric acid, sulfuric acid, and hydrochloric acid. Use of an organic acid or a mixture of an organic acid and a mineral acid is preferred, because it is believed that the peroxide may form a biocidal "per-acid" with the organic acid. The amount of pH adjusting agent present is dependent on the desired pH. Generally, for the pH adjusting agent should be present in an amount from about 0.5% to about 2.0% by weight of the composition.

The aqueous compositions of the present invention can also contain a pH control agent, or buffer, to ensure that the components of the composition remain soluble throughout the shelf life of the composition. Organic bases, such as amines, can be used, as can inorganic bases, such as sodium hydroxide and potassium hydroxide. Typically, the pH control agent is present in an amount from about 0 to about 3% by weight of the composition. The optimal amount will vary depending on the specific components of the composition.

The composition of the present invention may also comprise other additives, which may be any substance that enhances the composition with regard to (i) improved solubility or dispersion of other components, (ii) improved adhesion of the composition to the affected hoof area, (iii) control of wetting characteristics, and (iv) improved stability, which may be related to such properties as surface tension and viscosity, among other properties. The composition of the present invention may also comprise colorants, to provide a composition that is visible when applied, to ensure proper and complete application. The composition can further comprise agents, such as emollients, that act to decrease irritation to the skin caused by topical application.

Method

The present invention encompasses a method for the prevention or treatment of infectious diseases of the hoof in animals, comprising topically administering the aqueous composition of the present invention at or near the infected area. Preferably, the composition is used to treat PDD. The composition may be applied by pouring, squirting, flushing, sponging, or spraying it on or near the infected area, or by incorporating in a footwrap. In a preferred embodiment, the composition of the present invention are applied by spraying. Alternatively, the animal's hoof may be soaked, submerged, or immersed in the claimed compositions to effect treatment.

For the control and prevention of PDD, hoof rot, and stable hoof rot, the compositions can be used in a footbath through which the animals walk. Typically, the composition should be diluted with additional water; however the composition should not be diluted to such an extent that its germicidal ability can be fairly easily overcome by the harsh environmental conditions to which a foot bath is subjected, such as the presence of feces in the bath. For use in a foot bath, the compositions of the present invention can be diluted with water up to about 1000 times. Preferably, a 200-fold dilution is used.

Manufacture

The aqueous germicidal composition of the present invention can be made by conventional means. Preferably, the quaternary ammonium compound is added prior to the addition of the copper salt, and the peroxide should not be added until the copper salt is completely dissolved. After all the components are added, the composition should be mixed for an additional period of time to ensure complete dissolution of the copper salt and to achieve acceptable homogeneity.

The present invention is illustrated by the following Examples. These examples are illustrative of aqueous germicidal compositions and methods of the present invention and are not to be construed as limitations on the scope of the invention.

EXAMPLE 1

The aqueous composition of Example 1 was made by mixing the components in the following order:

| Material | % By Weight |
|---|---|
| Water | 69.9% |
| Hydroxyacetic acid | 0.5% |
| Barlox 12 (surfactant) | 1.0% |
| BTC 2125M (quaternary) | 1.0% |
| 75% Phosphoric acid | 0.6% |
| Copper sulfate pentahydrate | 20.0% |
| 35% Hydrogen peroxide | 10.0% |
| Total: | 100% |

The above composition had a pH in the range of 1.6 to 2.0, and a viscosity of 7.0 centipoises.

EXAMPLE 2

The aqueous composition of Example 2 was made by mixing the components in the following order:

| Raw Material | % By Weight |
|---|---|
| Water | 76.1% |
| Natrosol 250 MR-CS | 0.2% |
| 50% NaOH | 0.1% |
| BTC 2125M | 1.0% |
| Barlox 12, 30% | 1.0% |
| Hydroxyacetic acid | 0.5% |
| 75% Phosphoric acid | 1.0% |
| Copper sulfate pentahydr. | 15.0% |
| 35% hydrogen peroxide | 5.0% |
| FD&C Blue #1 | 0.1% |
| Total: | 100% |

The above composition had a pH in the range of 1.6 to 2.0, a viscosity of 4–6 centipoises, and was extremely storage stable.

EXAMPLE 3

The composition of Example 1 was then tested in the field with dairy cows infected with PDD. A total of 66 cows having PDD in various levels of severity were treated with either the composition of Example 1, or other commercially available compositions, using oxytetracycline as a positive control, and water as a negative control. Before treatment began, each cow was evaluated with respect to lesion size, lesion location, lesion appearance, dermatitis and pain. The compositions were sprayed on the infected areas of the hoof for the first week, and once on each of Monday, Wednesday, and Friday of the second week. During the two weeks of treatment, and for approximately two weeks, thereafter, each animal was examined and evaluated with respect to the above factors. A lesion improvement percentage was then determined based on the evaluation of lesion size, and pain with a positive lesion percentage change indicating improvement, and a higher positive change indicating greater improvement than a lesser positive change. The results are shown below in Tables I & II:

TABLE I

| | Two Week Evaluation | | | | |
|---|---|---|---|---|---|
| Treatment Group | No. Cows | No Pain | Pain | Sensitive | Lesion % Ch. |
| (1) Example 1 Composition | 14 | 12(86%) | 0 | 2(14%) | +68% |
| (2) CuSO$_4$ | 10 | 1(10%) | 9(90%) | 0 | +6% |
| (3) 27.5% H$_2$O$_2$ and 5.8% peracetic acid | 10 | 0 | 10(100%) | 0 | 0% |
| (4) 0.5% ionized CuSO$_4$ | 11 | 1(9%) | 10(91%) | 0 | +5% |

TABLE I-continued

<table>
<tr><td colspan="6">Two Week Evaluation</td></tr>
<tr><td>Treatment Group</td><td>No. Cows</td><td>No Pain</td><td>Pain</td><td>Sensitive</td><td>Lesion % Ch.</td></tr>
<tr><td>(5) Oxytetracycline<br>(25 mg/ml)</td><td>11</td><td>10(91%)</td><td>0</td><td>1(9%)</td><td>+67%</td></tr>
<tr><td>(6) Water</td><td>10</td><td>0</td><td>10(100%)</td><td>0</td><td>-11%</td></tr>
</table>

TABLE II

<table>
<tr><td colspan="6">30 Day Evaluation</td></tr>
<tr><td>Treatment Group</td><td>No. Cows</td><td>No Pain</td><td>Pain</td><td>Sensitive</td><td>Lesion % Ch.</td></tr>
<tr><td>(1) Example 1 Composition</td><td>13</td><td>10(77%)</td><td>1(8%)</td><td>2(15%)</td><td>+74%</td></tr>
<tr><td>(2) CuSO$_4$</td><td>10</td><td>2(20%)</td><td>7(70%)</td><td>1(10%)</td><td>+17%</td></tr>
<tr><td>(3) 27.5% H$_2$O$_2$ and 5.8% peracetic acid</td><td>10</td><td>0</td><td>10(100%)</td><td>0</td><td>0%</td></tr>
<tr><td>(4) 0.5% ionized CuSO$_4$</td><td>10</td><td>0</td><td>10(100%)</td><td>0</td><td>-5%</td></tr>
<tr><td>(5) Oxytetracycline (25 mg/ml)</td><td>10</td><td>8(80%)</td><td>2(20%)</td><td>0</td><td>+68%</td></tr>
<tr><td>(6) Water</td><td>8</td><td>0</td><td>8(100%)</td><td>0</td><td>-14%</td></tr>
</table>

The results show that the composition of the Example 1 was significantly more effective in treating PDD than were the comparative compositions, with the exception of oxytetracycline. With respect to oxytetracycline, the composition of Example 1 was just as effective in treating PDD.

EXAMPLE 4

The compositions of Example 1 and Example 2 were tested in the field with dairy cows infected with PDD. A total of 50 cows having PDD in various levels of severity were treated with either of the compositions of Example 1, the composition of Example 2, oxytetracycline, a composition comprising 27.5% hydrogen peroxide and 5.8% peracetic acid or water. Oxytetracycline was used as the positive control and water was used as the negative control. Before treatment began, each cow was evaluated with respect to lesion size, lesion color, and pain, and an initial lesion score was calculated. The lesion score was calculated by assigning numbers to lesion size (0–2), lesion color (1–4), and pain (0–2), with a larger number indicating a more severe condition. The cows were then divided into test groups, and an average lesion score for each test group was calculated. The compositions were sprayed on the infected areas of the hoof once daily for the first week, and once daily for four consecutive days in the second week. Two weeks after treatment was discontinued, the cows were evaluated with respect to the above factors. An average lesion score was determined for each test group, and an lesion score percentage improvement was determined by subtracting the post-treatment average lesion score from the pretreatment average lesion score, dividing that number by the pretreatment average lesion score. The results are shown below in Tables III and IV:

TABLE III

<table>
<tr><td>Treatment Group</td><td>No. Cows</td><td>No Pain</td><td>Pain</td><td>Lesion score (% change)</td></tr>
<tr><td>(1) Example 1 Composition</td><td>10</td><td>10(100%)</td><td>0</td><td>+67%</td></tr>
<tr><td>(2) Example 2 Composition</td><td>11</td><td>11(100%)</td><td>0</td><td>+65%</td></tr>
<tr><td>(3) Oxytetracycline</td><td>13</td><td>13(100%)</td><td>0</td><td>+64%</td></tr>
<tr><td>(4) 27.5% H$_2$O$_2$ 5.8% peracetic acid</td><td>8</td><td>0</td><td>8(100%)</td><td>-6%</td></tr>
<tr><td>(5) Water</td><td>8</td><td>0</td><td>8(100%)</td><td>-8%</td></tr>
</table>

TABLE IV

<table>
<tr><td rowspan="2">Treatment Group</td><td rowspan="2">No. Cows</td><td colspan="2">Average Lesion Score</td></tr>
<tr><td>Pre-Treatment</td><td>Post-Treatment</td></tr>
<tr><td>(1) Example 1 Composition</td><td>10</td><td>6</td><td>2</td></tr>
<tr><td>(2) Example 2 Composition</td><td>11</td><td>6</td><td>2.09</td></tr>
<tr><td>(3) Oxytetracycline</td><td>13</td><td>6</td><td>2.15</td></tr>
<tr><td>(4) 27.5% H$_2$O$_2$ 5.8% peracetic acid</td><td>8</td><td>5.88</td><td>6.25</td></tr>
<tr><td>(5) Water</td><td>8</td><td>5.88</td><td>6.38</td></tr>
</table>

The results show that the Example 1 and Example 2 compositions were as effective as oxytetracycline in treating PDD, and were considerably more effective than the hydrogen peroxide/peracetic acid composition or the negative control (water).

EXAMPLE 5

The composition of Example 1 was tested against commercially available compositions to determine its efficacy against *Fusobacterium necrophum*, a bacteria that causes hoof rot. The compositions were tested first in undiluted form against a predetermined concentration of the bacteria, in both a tube and plate assay. The compositions were then assayed in increasingly diluted form, until the point was reached where the diluted compostion no longer inhibited bacterial growth. This point is called the minimum inhibitory concentration, or "MIC," and is given as number, N, where N-1 represents the number of doubling dilutions that were made before the compostion failed to inhibit bacterial growth. For example, an MIC of 4 means that three doubling dilutions were made, so that the final dilution was 1:8. Thus, the dilution corresponding to the MIC is given by the formula $D=2^{N-1}$, where D is the amount of dilution and N is the MIC number. As stated above, the compositions were subjected to a tube assay and a plate assay. The tube assay is considered to be more precise and standardized, while the plate assay more accurately emulates the high organic load conditions found in a footbath.

The results against *Fusobacterium necrophorum* are set forth below in Table V, with a compostion having a higher MIC number having more germicidal efficacy in the test than a compostion having a lower MIC number. The number in parentheses indicates the number of times a particular assay was run.

TABLE V

| Composition | Tube Assay MIC | Plate Assay MIC |
| --- | --- | --- |
| Example 1 | 14(3) | 13(3) |
| Example 2 | | 12(1) |
| 0.5% ionized copper sulfate | 7(2) | 7(1) |
| 27.5% hydrogen peroxide | | |
| 5.8% peracetic acid | 12(3) | 11(2) |
| Quaternary ammonium compound and amphoteric surfactants | 13(1) | |
| Zinc sulfate | | 4(1) |
| limonene and surfactants | | 4(1) |
| 5% copper sulfate | 12(1) | 10(1) |
| 5% copper sulfate granules | 8(1) | 7(3) |
| 5% paraformaldehyde | | 4(1) |
| Lincomycin | 11(1) | |

EXAMPLE 6

The tests of Example 4 were repeated against *Dichelobacter nodosus*, an organism that is believed to cause hoof rot and stable hoof rot. The results are shown below in Table VI.

TABLE VI

| Composition | Tube Assay MIC | Plate Assay MIC |
| --- | --- | --- |
| Example 1 | 14(1) | 13(3) |
| 0.5 ionized copper sulfate | | 5(1) |
| 27.5% hydrogen peroxide | | 8(1) |
| 5.8% peracetic acid | | |
| Quaternary ammonium compound and amphoteric surfactants | | 14.5(1) |
| 5% paraformaldehyde | | 2(1) |

We claim:

1. An aqueous germicidal composition for the treatment or prevention of infectious diseases of the hoof in animals, comprising a copper salt, a quaternary ammonium compound, and a peroxide.

2. The composition of claim 1, where the pH of the composition is less than about 3.

3. The composition of claim 1, where the copper salt is present in an amount from about 2% to about 20% by weight of the solution, the quaternary ammonium compound is present in an amount from about 0.5 to about 2% by weight of the composition, and the peroxide is present in an amount from about 0.5% to about 5% by weight of the composition.

4. The composition of claim 3, where the copper salt is present in an amount from about 15% to about 20% by weight of the composition, the quaternary ammonium compound is present in an amount from about 1% to about 2% by weight of the composition, and the peroxide is present in an amount from about 1% to about 4% by weight of the composition.

5. The composition of claim 1, where the copper salt is copper sulfate.

6. The composition of claim 5, where the quaternary ammonium compound is at least one of trialkyl benzyl ammonium chloride, where the benzyl group can be substituted or unsubstituted.

7. The composition of claim 6, where the peroxide is hydrogen peroxide.

8. The composition of claim 1, further comprising a pH adjusting agent.

9. The composition of claim 8, further comprising a pH control agent.

10. The composition of claim 9, further comprising a surfactant.

11. The composition of claim 10, further comprising a viscosity enhancing agent.

12. An aqueous germicidal composition for the treatment or prevention of infectious diseases of the hoof in animals, comprising (a) from about 15% to about 20% copper sulfate by weight of the composition, (b) from about 0.5% to about 2% by weight of the composition of a quaternary ammonium compound comprising at least one trialkyl benzyl ammonium chloride, where the benzyl group can be substituted or unsubstituted, and (c) from about 1% to about 4% hydrogen peroxide by weight of the composition, where the pH of the composition is less than about 3.

13. A method for treating or preventing infectious diseases of the hoof in animals, comprising topically administering an effective amount of an aqueous germicidal composition comprising a copper salt, a quaternary ammonium compound, and a peroxide.

14. The method of claim 13, where the disease is papillomatous digital dermatitis.

15. The method of claim 13, where the copper salt is present in an amount from about 2% to about 20% by weight of the composition, the quaternary ammonium compound is present in an amount from about 0.5% to about 2% by weight of the composition, and the peroxide is present in an amount from about 0.5% to about 5% by weight of the composition.

16. The method of claim 15, where the disease is papillomatous digital dermatitis.

17. The method of claim 15, where the disease is hoof rot.

18. The method of claim 15, where the disease is stable hoof rot.

19. The method of claim 13, where the copper salt is of copper sulfate, the quaternary ammonium compound comprises at least one trialkyl benzyl ammonium chloride, where the benzyl group is substituted or unsubstituted, and the peroxide is hydrogen peroxide.

20. The method of claim 13, where the copper salt is present in an amount from about 15% to about 20% by weight of the composition, the quaternary ammonium compound is present in an amount from about 1% to about 2% by weight of the composition, and the peroxide is present in an amount form about 1% to about 4% by weight of the composition.

21. The method of claim 20, where the disease is papillomatous digital dermatitis.

22. The method of claim 20, where the disease is hoof rot.

23. The method of claim 20, where the disease is stable hoof rot.

24. The method of claim 13, where the composition is administered as a spray.

25. The method of claim 13, where the composition is administered as a footbath.

26. A method for treating or preventing infectious diseases of the hoof in animals, comprising topically administering an effective amount of an aqueous germicidal composition comprising, (a) from about 15% to about 20% copper sulfate by weight of the composition, (b) from about 0.5% to about 2% by weight of the composition of a quaternary ammonium compound comprising at least one trialkyl benzyl ammonium chloride, where the benzyl group is substituted or unsubstituted, and (c) from about 1% to about 4% hydrogen peroxide by weight of the composition, where the pH of the composition is less than about 3.

27. The method of claim 26, where the disease is PDD.

28. The method of claim 26, where the disease is hoof rot.

29. The method of claim 26, where the disease is stable hoof rot.

* * * * *